United States Patent [19]
Zupanick

[11] Patent Number: 4,995,198
[45] Date of Patent: Feb. 26, 1991

[54] METHOD FOR MAKING A REFLECTANCE CALIBRATION PLATE HAVING A NEAR-LAMBERTIAN SURFACE

[75] Inventor: Joseph E. Zupanick, Richardson, Tex.

[73] Assignee: Atlantic Richfield Company, Los Angeles, Calif.

[21] Appl. No.: 651,023

[22] Filed: Sep. 17, 1984

[51] Int. Cl.$^5$ .............................................. B24C 1/00
[52] U.S. Cl. .................................... 51/319; 356/243
[58] Field of Search .............. 51/319, 320, 321, 410; 356/243; 350/252.1

[56] References Cited

U.S. PATENT DOCUMENTS

| 1,566,127 | 12/1925 | Rundquist | 51/319 |
| 4,047,032 | 9/1977 | Judge et al. | 356/243 |

FOREIGN PATENT DOCUMENTS

| 0072598 | 6/1979 | Japan | 51/319 |
| 0090825 | 7/1980 | Japan | 356/243 |

OTHER PUBLICATIONS

"Reflectivity Reference Standard for Toner Concentration Sensor"; IBM Tech. Disclosure Bulletin; K. L. Bilby; vol. 21; No. 6; 11/1978.

"Long Term Calibration Standard for Submicron Air Gaps" IBM Tech. Disclosure Bulletin; H. E. Korth; vol. 22; No. 3; 8/1979.

"Reflectance and Transmission Standards"; Diano Corporation Price List; 7/1970.

Primary Examiner—Robert A. Rose
Attorney, Agent, or Firm—James H. Phillips; Michael E. Martin

[57] ABSTRACT

In order to provide an optical reflectivity test plate for calibrating and proving a radiometer, which test plate exhibits a near-Lambertian surface, a ceramic coating is bonded to a surface of a rigid substrate, such as a steel plate, and the ceramic coating is thereafter sandblasted with a fine abrasive (preferably 60 grit or finer). If ordinary silica or other relatively soft abrasive is employed in the sandblasting step, it must not have have been previously used. Test procedures for comparing the resultant test plates to a standard BaSO$_4$ test plate in both the laboratory and outdoors are given.

9 Claims, 2 Drawing Sheets

METHOD FOR MAKING A REFLECTANCE CALIBRATION PLATE HAVING A NEAR-LAMBERTIAN SURFACE

FIELD OF THE INVENTION

This invention relates to the testing and measurement arts and, more particularly, to a standard test plate for calibrating the response of a radiometer adapted to measure light reflectance, from an illuminated target object, in and near the visible range of the spectrum. This invention further relates to methods for making such test plates.

BACKGROUND OF THE INVENTION

Optical instruments which measure target reflectance are employed to indirectly determine diverse characteristics of targets within the field of view. For example, the device set forth in U.S. Pat. No. 3,598,994, upon which is based the famous Fraunhofer Line Discriminator (FLD) used for some years by the United States Geological Survey at Flagstaff, Ariz., measures, separately, (a) reflectance within and (b) apparent reflectance adjacent a selected Fraunhofer band to obtain a measurement of luminescence in the Fraunhofer band issuing from a target under stimulation by direct sunlight. A handheld optical instrument for obtaining like measurements, but employing a different technological implementation approach, is disclosed in copending U.S. patent application Ser. No. 509,681, filed May 30, 1983, by Robert D. Watson for "Portable Luminescence Sensor". Certain observation and meteorological satellite systems measure upwelling radiances at several wavelengths and telemeter the data to ground stations. The measurements obtained with these instruments and systems may be analyzed to classify target spectral characteristics from which mineralogical, geological, and other target information can be deduced, often in conjunction with target characteristics obtained from still other measurements taken with other instruments.

In order to achieve the necessary measurement accuracy, those skilled in the art will appreciate that instruments of the contemplated type which are carried by aircraft or by hand must be very closely calibrated, not only in the laboratory, but also in the field. Such calibration requires the use of a standard target illuminated by (at least in the laboratory) a standard light source directed onto the target from which a predetermined measurement by the instrument under proof should be obtained. Any deviation from the expected measurement may be used to recalibrate the instrument, derive coefficients involved in the equations for reflectance and luminescence, and/or develop correction factors to be applied to the instrument readings taken in the field. Once a close laboratory calibration has been achieved, it is possible to readjust (or revise the correction factors applied to) an instrument in the field if a reliable standard test target is available.

Both standard illuminants and standard reflectance test targets are well known. Illuminants generally contain energy at many wavelengths, therefore, they must be considered in terms of an energy distribution curve showing the intensity at each wavelength rather than in terms of a single number. Different spectral distributions give a different appearance to the same object. To standardize this variable, several reference illuminants have been established by the CIE (Commission Internationale de l'Eclairage), and the spectral distributions of these illuminants have been accurately determined and published. By way of example, a tungsten filament lamp, operating with a specified voltage and current, will have a color temperature of 2854 K and possesses known energy at each wavelength. This illuminant is identified as the standard CIE Illuminant A which possesses known energy at each wavelength.

It is desirable, usually even necessary, for reflectance standards to have surfaces exhibiting a near Lambertian characteristic. Lambert defined a perfectly diffuse surface (commonly designated as a Lambertian surface) as one for which the radiance is constant for any angle of reflection to the surface normal. For purposes of simplification, the term "Lambertian surface", as used herein, shall, for practical purposes, actually mean a nearLambertian surface. The most commonly used reflectance standards exhibiting Lambertian surfaces are painted barium sulfate ($BaSO_4$) test plates which may have been, in turn, calibrated against a pressed $BaSO_4$ or "Halon" (registered trademark of the Eastman-Kodak Co.) powder disc (or another known standard which may have been certified by the National Bureau of Standards) to refine the known accuracy of a given specimen. Painted $BaSO_4$ plates have two distinct drawbacks which are notoriously well known in the art; viz.: they are very delicate and they are costly. "Halon" discs (which may be obtained from Eastman-Kodak) are not appropriate for field use because they can only be obtained in a two-inch diameter size.

OBJECTS OF THE INVENTION

It is therefore a broad object of my invention to provide an improved test target for calibrating a reflectance radiometer.

It is another broad object of my invention to provide an improved reflectance standard for calibrating a reflectance radiometer.

It is a more specific object of my invention to provide such a standard in the form of a test plate which is invariant with time and is sturdy and reliable for use in the laboratory and in the field and which may be readily and economically fabricated.

It is a further specific object of my invention to provide such a test plate which has reflective surfaces exhibiting the Lambertian characteristic.

SUMMARY OF THE INVENTION

Briefly, these and other objects of the invention are achieved by bonding a ceramic coating to a surface of a rigid substrate, such as a steel plate, and sandblasting the ceramic coating with a fine abrasive (preferably 60 grit or finer) which, if ordinary silica or other relatively soft abrasive, has not been previously used to thereby obtain a test plate which exhibits a near-Lambertian characteristic and which may be employed as a standard for calibrating and for proving a radiometer.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the accompanying drawing of which:

DETAILED DESCRIPTION OF THE INVENTION

Figure 1:
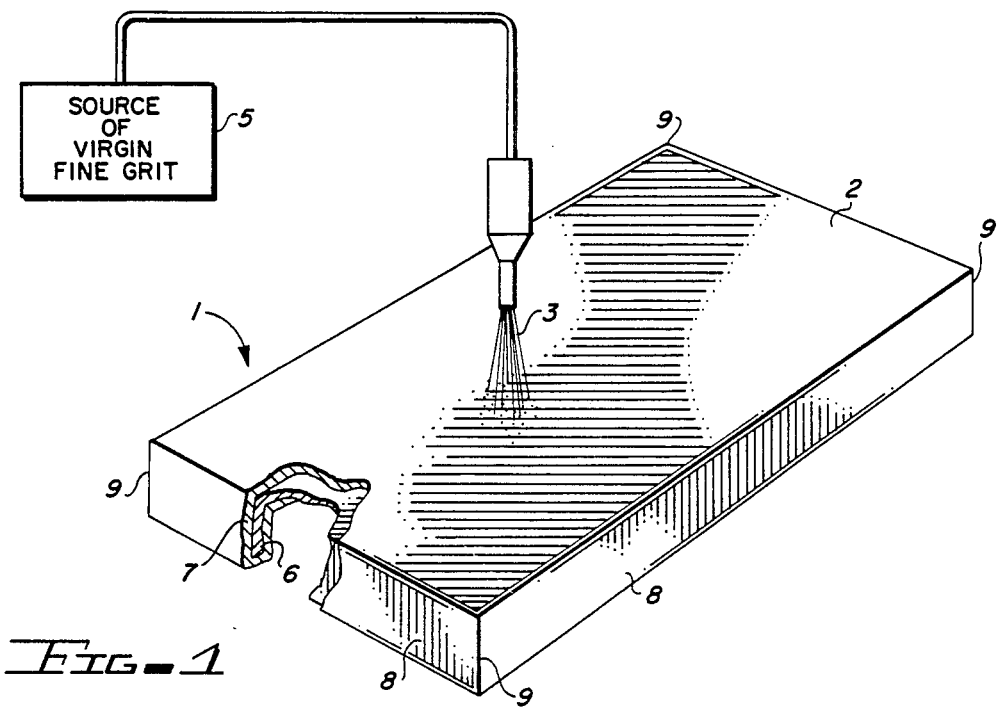
FIG. 1 is a pictorial view illustrating the sandblasting step employed in producing a test plate which is shown partially cutaway.

Referring now to FIG. 1, a test plate 1 is illustrated in the process of having its upper surface 2 prepared to take on Lambertian characteristics which are imparted by the effect of abrasive 3 issuing from sandblaster nozzle 4 to impinge upon the upper surface 2. The abrasive 3 is supplied from a source 5 of fine grit. Preferably, the grit from the source 5 should be at least 60 fine, and particularly good results have been achieved with grit as fine as 240. It is speculated that the particle size might usefully be on the order of the wavelength of interest. It is especially important to note that the grit, if common silica, must not have previously been used; experience has shown that silica abrasive which has made only a single pass through the sandblaster will not produce the desired Lambertian surface. Tougher abrasive grit, such as silicon carbide, may be effective through more than a single use, but it is believed that the best results are nonetheless obtained with virgin abrasive. Angular, not rounded, pits are sought.

As shown in the cutaway portion of the test plate 1 illustrated in FIG. 1, the test plate may usefully comprise a steel plate substrate 6 overlaid on all surfaces with a ceramic coating 7 of which the upper surface 2 receives the sandblasting treatment. In order to achieve rigidity in conjuction with relative light weight, the edges 8 (and the corresponding edges out of view in FIG. 1) may be bent downwardly at a 90° angle and joined at the corners 9 to realize the desired rigid structure.

The methods for bonding ceramic coatings to a rigid substrate are well known in the art and need not be treated at length in this specification other than to note that the process generally involves overlaying all surfaces of the rigid substrate with a coating of prepared ceramic paste, which may include material to enhance the bonding process, and subjecting the plate to high temperatures for a sufficient length of time to allow the ceramic material to fuse and adhere to the substrate. All surfaces of the substrate are usually coated because the substrate and coating have different coefficients of expansion with temperature which could lead to a warped end product on cool down if only a single surface were coated. The thickness of the ceramic coating should be adequate to insure that the surface spectral characteristics are not altered when material is removed by the subsequent sandblasting step.

It is useful to note that reflectance test plates comprising glazed ceramic overlaying a steel substrate and exhibiting selected coefficients of reflectivity are commercially available. These commercially available products, however, have a full glossy surface rather than a Lambertian surface. These commercially available test plates may nonetheless be directly subjected to the sandblasting process illustrated in FIG. 1 to obviate the necessity for preparing the test plates prior to treatment of the surface. By way of example, such standard reflectance test plates having ceramic surfaces which may be transformed into Lambertian surfaces in accordance with the present invention may be obtained from Erie Ceramic Arts Co., 3120 W. 22nd St., Erie, Pa. 16505.

Another source of test plates which do not initially exhibit a Lambertian surface, but which can be treated in accordance with the sandblasting process discussed above, are ceramic tiles such as those available from the Corning Glass Company under the registered trademark "Corningware". Again, the tiles, as commercially available, carry a glossy, non-Lambertian surface, but such surfaces have been found to be amenable to treatment by sandblasting with virgin grit to take on the desired Lambertian characteristic.

TEST PROCEDURE

In order to determine whether test plates in accordance with the present invention do exhibit the necessary Lambertian characteristic, a series of tests were conducted both in the laboratory and outdoors against a standard comprising a $BaSO_4$ test surface.

Figure 2:
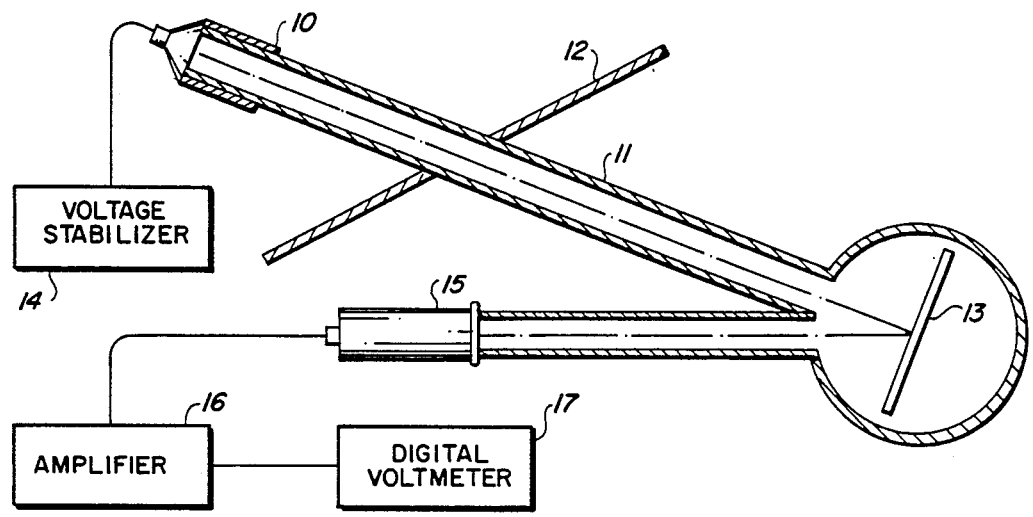
FIG. 2 is a pictorial illustrating a laboratory setup for comparing test plates in accordance with the present invention with a prior art $BaSO_4$ test plate.

The measurement setup used in the laboratory is shown in FIG. 2. The light beam from a spotlight 10 placed approximately nine feet from the surface to be measured was defined by a pipe 11 having a blackened interior and a baffle plate 12 so that an area only four inches in diameter was illuminated in the plane of the sample 13. The uniformity of illumination within the four inch area was determined to be better than 98%. (A conventional autocollimation procedure was used to insure the correct measurement geometry.) The spotlight 10 was energized from a voltage stabilized power source 14 to avoid light intensity changes caused by line voltage fluctuations.

A radiometer 15 responded to impinging light by issuing a proportional low level voltage signal which was amplified by amplifier 16 to a range readily displayed by a digital voltmeter 17. It should be noted that the spatial responsivity of the radiometer used has a significant effect on the measurement. If a radiometer which has poor spatial responsivity (i.e., poor out-of-field rejection characteristics) is employed, the emission and reflection of the sample surroundings will contribute significantly to the measured signal. This gives rise to measurement errors. The radiometer used was selected to have an excellent spatial responsivity which suppressed the effect of surroundings on the laboratory measurements to a level of 0.5% of the readings for high reflectance surfaces.

It is believed that any residual errors in the laboratory measurements were attributable primarily to the relative comparison of the reference to the samples and the uncertainty in the reference itself. The reference, a $BaSO_4$ plate, was calibrated with respect to a "Halon" disc calibrated by and obtained from the Eastman Kodak Company in early 1983. The calibration results for the $BaSO_4$ plate are given in Table 1. The total measurement error is estimated at about 1% on the average.

TABLE 1

| The Reflectance of the Reference $BaSO_4$ Surface. | | | | |
| --- | --- | --- | --- | --- |
| | | Irradiance | | |
| alpha (deg) | 450 nm | 550 nm | 650 nm | 850 nm |
| 10 | 0.880 | 0.877 | 0.874 | 0.884 |

TABLE 1-continued

| | The Reflectance of the Reference BaSO₄ Surface. | | | |
|---|---|---|---|---|
| | Irradiance | | | |
| alpha (deg) | 450 nm | 550 nm | 650 nm | 850 nm |
| 15 | 0.877 | 0.875 | 0.866 | 0.875 |
| 20 | 0.874 | 0.872 | 0.863 | 0.871 |
| 25 | 0.867 | 0.865 | 0.860 | 0.868 |
| 30 | 0.859 | 0.855 | 0.854 | 0.864 |
| 35 | 0.850 | 0.844 | 0.844 | 0.857 |
| 40 | 0.844 | 0.832 | 0.838 | 0.850 |
| 50 | 0.808 | 0.808 | 0.816 | 0.829 |
| 55 | 0.781 | 0.782 | 0.800 | 0.816 |
| 60 | 0.768 | 0.757 | 0.776 | 0.793 |

Calibrated data: Sept. 13. 1983
location: Infrared Lab., OSC University of Arizona
The field of view of radiometer = 1 degree
   The wavelength intervals of filters:
   450 ± 20 nm
   550 ± 20 nm
   650 ± 20 nm
   850 ± 20 nm
   Reference: Calibrated "Halon"

Those skilled in narrow aspects of the art will recognize the filter nominal wavelengths as corresponding to Landsat thematic mapper wavelengths.

Figure 3:
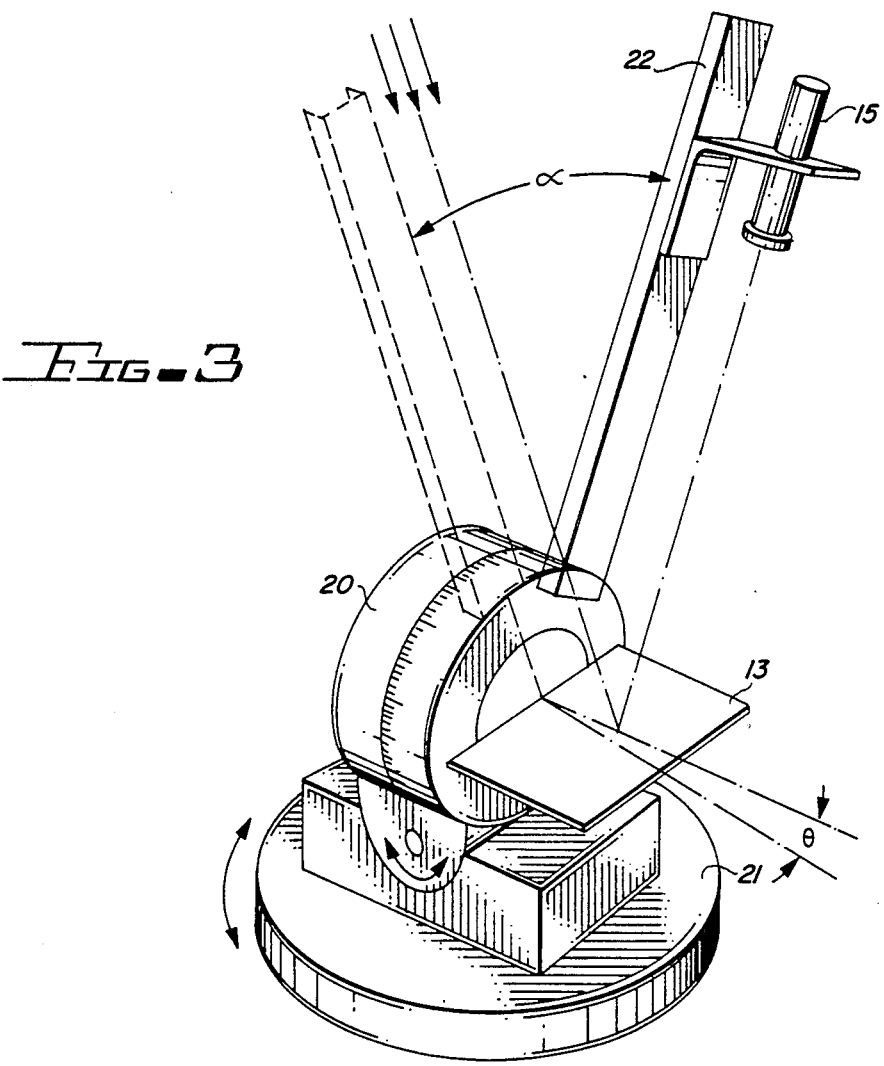
FIG. 3 is a pictorial illustrating a field setup for comparing test plates in accordance with the present invention with the prior art $BaSO_4$ test plate in the presence of sunlight.

The samples were also measured outdoors for which the setup is illustrated in FIG. 3. To keep the measurement conditions similar to those of the laboratory measurements, an ordinary machine shop divider, rotatable upon a base 21 and able to both tilt forward and change in azimuth angle, was employed. The tilting angle, theta, was adjustable to ensure that the sun's direction was normal to the sample 13. The radiometer 15 was of necessity attached to the rotating arm 22 so that it viewed the sample surface only in the principal plane of the sun. (It may be noted that another acceptable test procedure involves undertaking to fix the radiometer field of view normal to the test sample and illuminating the sample from a measurable angle. The alternative procedures yield substantially the same results because reciprocity is valid.)

Before each outdoor measurement was taken, a boresighted box with two holes on opposite sides was put onto the sample holder to determine if the surface was normal to the sun's rays. Then a sample and the reference BaSO₄ disc were placed on the sample holder in as rapid succession as possible, and two readings, $V_{TS}$ and $V_{TR}$ respectively, were recorded. With an opaque plate shielding an area covering the samples and reference disc from direct sunlight, two additional readings, $V_{dS}$ and $V_{dR}$, were recorded. The reflectance of the sample was given by:

$$R_{(sample)}^* = ((V_{TS} - V_{dS})/V_{TR}) - V_{dR})R_{(reference)}^*$$

(* indicates at a selected angle and wavelength)
where
   $V_{TS}$ was the voltage reading when the sample was measured under total irradiance (direct + diffuse irradiance),
   $V_{TR}$ was the voltage reading when the reference was measured under total irradiance,
   $V_{dS}$ was the voltage reading when the sample was shielded with a plate and only diffuse irradiance illuminated the sample,
   $V_{dR}$ was the voltage reading when the reference was shielded with a plate and only diffuse irradiance illuminated the reference.

The radiometer was tilted from an angle of 10 degrees to the normal to an angle of 60 degrees to the normal in 5 degree increments. At each increment, a set of four voltage readings was taken for each sample in order.

Figure 4:
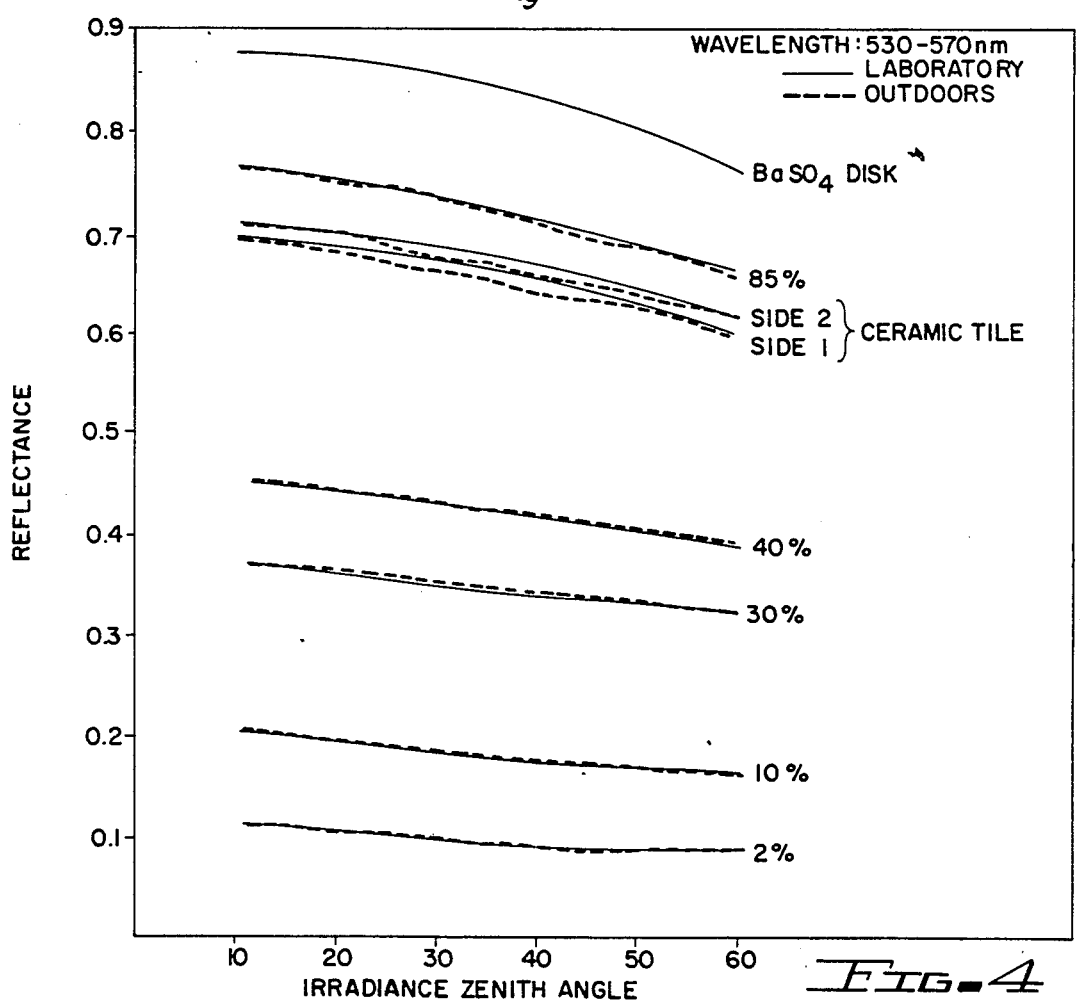
FIG. 4 is a graphic presentation of the results obtained with the setups shown in FIGS. 2 and 3.

Five standard reflectance plates (each comprising a ceramic coating over a steel substrate) having respective as fabricated nominal reflectance ratings of 2%, 10%, 30%, 40%, and 85% were obtained from Erie Ceramic and treated by sandblasting the standard reflective upper surface with virgin silica fine abrasive as set forth above. In addition, a ceramic "Corningware" title was obtained and similarly treated on both sides. FIG. 4 shows how the reflectance of the samples and the standard BaSO₄ surface varied with irradiance zenith angle. The solid lines are for the data taken in the laboratory, and the dashed lines are for the data collected outdoors after the diffused component was subtracted out.

Comparison of the results of medium and high reflectance measurements made in the laboratory and outdoors show good agreement with average differences on the order of 1%. Accurate outdoor measurements were found to be difficult to obtain due to the continual change of the solar zenith and azimuth angles and changes in atmospheric conditions. It has been pointed out (Robinson, B. F. and L. L. Biehl, "Calibration Procedures for the Measurement of Reflectance Factor in Remote Sensing Field Research." SPIE 196:16-26, 1979.) that canopy reflectance measurements which include skylight on a hazy day will differ from laboratory measurements by a systematic 3% for the spectral band from 0.5 to 0.6 μm. The main factors affecting the measurement are skylight and the extent by which the sample departs from Lambertian characteristics. For the measurements presented, a clear-sky day was chosen, and the samples had approximately Lambertian characteristics. The effect of skylight on the measurement was also taken into account. For example, if the subtraction method to eliminate the effect of skylight had not been used; i.e., reflectance had been calculated from $V_{TS}/V_{TR} \times R_T$, there would have been a difference of 11.5% for the 2% plate at an irradiance angle of 60'. The lower the reflectance and/or the stronger the diffuse light from the hemispheric sky, the larger the error.

The measurement of a black velvet sample (commercially available from Edmund Scientific) provided a good example of the increase in reflectance differences. The black velvet had an extremely low reflectance (about 0.0055 on average). When measured, because the surround had higher reflectance and was of much larger area than the sample, the out-of-field-of-view irradiance became a substantial proportion of the total irradiance. It was observed that the signal voltage due to the direct component within the sample area accounted for only 10% of the total. The effect of scattered irradiance and the change in cloud cover during the measurement contributed more to the results than they would have in the case of the measurement of higher reflectance surfaces. In contrast, the scattering component was found to be small and constant in the laboratory, and the measurements can be made more repeatedly and precisely.

It will be apparent from a study of FIG. 4 that the practice of the present invention results in sturdy and reliable test plates having near-Lambertian surfaces which are fully as usable as standards as is the fragile and costly BaSO₄ disc.

While the principals of the invention have now been made clear in illustrative embodiments, there will be immediately obvious to those skilled in the art many modifications of structure, arrangements, proportions, elements, materials, and components, used in the practice of the invention which are particularly adapted for specific environments and operating requirements without departing from these principals.

I claim:

1. A method for making a test plate having a reflective surface exhibiting a near-Lambertian characteristic comprising the steps of:

(A) bonding a ceramic coating to a surface of a rigid substrate, said ceramic coating being of sufficient thickness to prevent alteration of its surface spectral characteristics during the performance of step (B); and (B) sandblasting at least one surface of the ceramic coating employing a fine abrasive in such condition that angular, and not rounded, pits are obtained in the sandblasted ceramic surface.

2. The method of claim 1 in which the rigid substrate comprises a steel plate and in which the ceramic coating is bonded to all surfaces of said steel plate.

3. The method of claim 1 or 2 in which step (B) is carried out using a fine abrasive which has not been previously used.

4. The method of claim 3 in which step (B) is carried out using silica as the abrasive.

5. The method of claim 1 or 2 in which step (B) is carried out using silicon carbide as the abrasive.

6. A method for making a test plate having a reflective surface exhibiting near-Lambertian characteristics comprising the steps of:

(A) selecting a ceramic plate having at least one planar face; and (B) sandblasting the planar face employing a fine abrasive in such condition that angular, and not rounded, pits are obtained in the sandblasted ceramic planar face.

7. The method of claim 6 in which step (B) is carried out using a fine abrasive which has not been previously used.

8. The method of claim 7 in which step (B) is carried out using silica as the abrasive.

9. The method of claim 6 in which step (B) is carried out using silicon carbide as the abrasive.

* * * * *